US007514592B2

(12) United States Patent
Krieger et al.

(10) Patent No.: US 7,514,592 B2
(45) Date of Patent: Apr. 7, 2009

(54) INDUCIBLE HEART ATTACK ANIMAL MODEL

(75) Inventors: Monty Krieger, Needham, MA (US); Songwen Zhang, Cambridge, MA (US); Sharon L. Karackattu, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/099,343

(22) Filed: Apr. 5, 2005

(65) Prior Publication Data

US 2005/0223420 A1    Oct. 6, 2005

Related U.S. Application Data

(60) Provisional application No. 60/645,922, filed on Jan. 21, 2005, provisional application No. 60/559,926, filed on Apr. 5, 2004.

(51) Int. Cl.
*G01N 33/00*  (2006.01)
*A01K 67/00*  (2006.01)
*C12N 15/05*  (2006.01)

(52) U.S. Cl. .............................. 800/9; 800/18; 800/22; 800/25; 800/3

(58) Field of Classification Search ..................... 800/3, 800/8, 9, 13–18, 25
See application file for complete search history.

(56) References Cited

U.S. PATENT DOCUMENTS

| 3,625,214 | A | 12/1971 | Higuchi, et al. |
| 4,789,734 | A | 12/1988 | Pierschbacher |
| 4,906,474 | A | 3/1990 | Langer et al. |
| 4,925,673 | A | 5/1990 | Steiner et al. |
| 6,437,215 | B1 * | 8/2002 | Krieger et al. ............... 800/18 |
| 2002/0108131 | A1 | 8/2002 | Krieger et al. |
| 2002/0194628 | A1 * | 12/2002 | Weisgraber et al. ............ 800/8 |

FOREIGN PATENT DOCUMENTS

WO    WO 02074967    9/2002

OTHER PUBLICATIONS

Calrk et al. A Future for Transgenic Livestock. Nature Reviews: Genetics. Oct. 2003, vol. 4, pp. 825-833.*
Niemann et al. Transgeic Farm Animals: Present and Future. Rev. Sci, Tech. Off. Int. Spiz. 2005, vol. 24, pp. 285-298.*
Wheeler et al. Transgenic Technology and Applications in Swine. Theriogenology. 2001, vol. 56, pp. 1345-1369.*
Prelle et al. Pluripotent Stem Cells-Models of Embryonic Development, Tool for Gene Targeting, and Basis of Cell Therapy. Anat. Histol. Embryol. 2002, vol. 31, pp. 169-186.*
Trigatti et al. Influence of the High Density Lipoprotein Receptor SR-BI on Reproductive and Cariovascular Pathophysiology. Proc. Natl. Acad. Sci. 1999, Vol. 96, pp. 9322-9327.*
Denning et al. Gene Targeting in Primary Fetal Fibroblasts from Sheep and Pig. Cloning and Stem Cells. 2001, vol. 3, pp. 221-231.*
Wooddell et al. Long-Term RNA Interference from Optimized siRNA Expression Constructs in Adult Mice. Biochem. Biophys. Res. Comm. 2005, vol. 334, pp. 117-127.*
Sullivan et al. Type III Hyperlipoproteinemia and Spontaneous Atherosclerosis in Mice Resulting from Gene Replacement of Mouse ApoE with Human ApoE*2. Journal of Clinic. Invest. 1998, vol. 102, pp. 130-135.*
Braun, et al., "Loss of SR-BI expression leads to the early onset of occlusive atherosclerotic coronary artery disease, spontaneous myocardial infarctions, severe cardiac dysfunction, and premature death in apolipoprotein E-deficient mice", *Circ. Res.*, 90(3):270-6 (2002).
Braun, et al., "Probucol prevents early coronary heart disease and death in the high-density lipoprotein receptor SR-BI/apolipoprotein E double knockout mouse", *Proc. Natl. Acad. Sci. U.S.A.*, 100(12):7283-8 (2003).
Caligiuri, et al., "Myocardial infarction mediated by endothelin receptor signaling in hypercholesterolemic mice", *Proc. Natl. Acad. Sci. U.S.A.*, 96(12):6920-4 (1999).
Clark and Whitelaw, "A future for transgenic livestock", *Nat. Rev. Genet.*, 4(10):825-33 (2003).
Cooper, "Hepatic uptake of chylomicron remnants", *J. Lipid Res.*, 38(11):2173-92 (1997).
Dansky, et al., "T and B lymphocytes play a minor role in atherosclerotic plaque formation in the apolipoprotein E-deficient mouse", *Proc. Natl. Acad. Sci. U.S.A.*, 94(9):4642-6 (1997).

(Continued)

*Primary Examiner*—Deborah Crouch
(74) *Attorney, Agent, or Firm*—Pabst Patent Group LLP

(57) ABSTRACT

An animal model of coronary heart disease has been developed where myocardial infarct can be induced by altering the animal's diet. In all embodiments, this animal model is a result of reduced activity of scavenger receptor class BI (SR-BI) and apolipoprotein E (ApoE). In a preferred embodiment, the model is a result of crossbreeding two transgenic mouse lines: a knockout of SR-BI (SR-BI−/−) and an impaired ApoE expressor (hypoE). The impaired ApoE gene results in only 2-5% expression of ApoE and a reduction in cholesterol homeostasis. Resulting animals are predisposed to hypercholesterolemia but can live longer than a year on a normal low fat diet. Serum plasma levels can be significantly elevated by changing the animal's diet to one containing high levels of fat and cholesterol. Within a month on a high fat, high cholesterol diet, animals develop atherosclerosis and myocardial infarction occurs. Survival depends on the nature of the diet and the conditions of animal husbandry and can typically be around 20-30 days after administration of the modified diet depending on the specific conditions. Housing the animals alone or in groups significantly affects survival of these animals on a high fat diet. Analysis of B- and T-cell deficient SR-BI/ApoE/RAG2 triple knockout mice established that B- and T-lymphocytes do not play a key role in the pathophysiology of the SR-BI ApoE dKO model of human disease. These animal models can be used to study mechanisms and progression of CHD as a function of diet, treatment with drugs to be screened for efficacy or undesirable side effects, and social environmental effects.

16 Claims, 4 Drawing Sheets

OTHER PUBLICATIONS

Dorsett and Tuschl, "siRNAs: applications in functional genomics and potential as therapeutics", *Nat. Rev. Drug Discov.*, 3(4):318-29 (2004).

Gao, et al., "Serial echocardiographic assessment of left ventricular dimensions and function after myocardial infarction in mice", *Cardiovasc. Res.*, 45(2):330-8 (2000).

Gardin, et al., "Echocardiographic assessment of left ventricular mass and systolic function in mice", *Circ. Res.*, 76(5):907-14 (1995).

Kocher et al., "Targeted disruption of the PDZK1 gene in mice causes tissue-specific depletion of the high density lipoprotein receptor scavenger receptor class B type I and altered lipoprotein metabolism", *J. Biol. Chem*, 278(52)52820-5 (2003).

Liao, et al., "Echocardiographic assessment of LV hypertrophy and function in aortic-banded mice: necropsy validation", *Am. J. Physiol. Heart Circ. Physiol.*, 282(5)H1703-8 (2002).

Mahley and Ji, "Remnant lipoprotein metabolism: key pathways involving cell-surface heparan sulfate proteoglycans and apolipoprotein E", *J. Lipid Res.*, 40(1):1-16 (1999).

Miettinen, et al., "Abnormal lipoprotein metabolism and reversible female infertility in HDL receptor (SR-BI)-deficient mice", *J. Clin. Invest.*, 108(11):1717-22 (2001).

Nieland, et al., "Discovery of chemical inhibitors of the selective transfer of lipids mediated by the HDL receptor SR-BI", *Proc. Natl. Acad. Sci. U.S.A.*, 99(24):15422-7 (2002).

Nishimura, et al., "Autoimmune dilated cardiomyopathy in PD-1 receptor-deficient mice", *Science*, 291(5502):319-2 (2001).

Raffai, et al., "Introduction of human apolipoprotein E4 "domain interaction"into mouse apolipoprotein E", *Proc. Natl. Acad. Sci. U.S.A.*, 98(20):11587-91 (2001).

Raffai and Weisgraber, "Hypomorphic apolipoprotein E mice: a new model of conditional gene repair to examine apolipoprotein E-mediated metabolism", *J. Biol. Chem.*, 277(13)11064-8 (2002).

Reardon, et al., "Effect of immune deficiency of lipoproteins and atherosclerosis in male apolipoprotein E-deficient mice", *Arterioscler. Thromb. Vasc. Biol.*, 21(6):1011-6 (2001).

Rigotti, et al, "The role of high-density lipoprotein receptor SR-BI in the lipid metabolism of endocrine and other tissues", *Endocr. Rev.*, 24(3):357-87 (2003).

Rigotti, et al., "A targeted mutation in the murine gene encoding the high density lipoprotein (HDL) receptor scavenger receptor class B type I reveals its key role in HDL metabolism", *Proc. Natl. Acad. Sci. U.S.A.*, 94(23):12610-5 (1997).

Roselaar, et al., "Lymphocyte populations in atherosclerotic lesions of apoE -/- and LDL receptor -/- mice. Decreasing density with disease progression", *Arterioscler. Thromb. Vasc. Biol.*, 16(8):1013-8 (1996).

Roth, et al., "Impact of anesthesia on cardiac function during echocardiography in mice", *Am. J. Physiol. Heart Circ. Physiol.*, 282(6):H2134-40 (2002).

Tanaka, et al., "Transthoracic echocardiography in models of cardiac disease in the mouse", *Circulation*, 94(5):1109-17 (1996).

Takuma, et al., "Anesthetic inhibition in ischemic and nonischemic murine heart: comparison with conscious echocardiographic approach", *Am. J. Physiol. Heart Circ. Physiol.,*, 280(5):H2364-70 (2001).

Van Eck, et al., "Differentiial effects of scavenger receptor BI deficiency on lipid metabolism in cells of the arterial wall and in the liver", *J. Biol. Chem.*, 278(26):23699-705 (2003).

Weisgraber, "Apolipoprotein E: structure-function relationships", *Adv. Protein Chem.*, 45:249-302 (1994).

Yang, et al., "Echocardiographic assessment of cardiac function in conscious and anesthetized mice", *Am. J. Physiol.*, 277(5 Pt2):H1967-74 (1999).

Zimmer and Gruss, "Production of chimaeric mice containing embryonic stem (ES) cells carrying a homoeobox Hox 1.1 allele mutated by homologous recombination", *Nature*, 338(6211):150-3 (1989).

Zhang, et al., "Diet-induced occlusive coronary atherosclerosis, myocardial infarction, cardiac dysfunction, and premature death in scavenger receptor class B type I-deficient, hypomorphic apolipoprotein ER61 mice", *Circulation*, 111(25):3457-64 (2005).

Zhang, et al., "Inactivation of macrophage scavenger receptor class B type I promotes atherosclerotic lesion development in apolipoprotein E-deficient mice", *Circulation*, 108(18):2258-63 (2003).

* cited by examiner

INDUCIBLE HEART ATTACK ANIMAL MODEL

CROSS-REFERENCE TO RELATED APPLICATIONS

This application claims priority to U.S. Ser. No. 60/559,926 filed Apr. 5, 2004 and U.S. Ser. No. 60/645,922 filed Jan. 21, 2005.

STATEMENT OF FEDERALLY SPONSORED SUPPORT

The U.S. government has certain rights to this invention by virtue of Grants HL64737 and HL66105 from the National Institutes of Health-National Heart, Lung and Blood Institute to Monty Krieger.

BACKGROUND OF THE INVENTION

This invention is generally in the area of a transgenic animal model that can be induced to have heart attacks for studying coronary heart disease and assaying novel treatments for coronary heart disease.

Coronary heart disease (CHD) is the most common form of heart disease, the leading cause of death in the United States. About 12.6 million Americans suffer from CHD, which often results in a heart attack. Each year, about 1.1 million Americans suffer a heart attack and 515,000 of these heart attacks are fatal. One of the risk factors for developing CHD is elevated blood cholesterol. As blood cholesterol rises, so does risk of coronary heart disease. When other risk factors (such as high blood pressure and tobacco smoke) are present, this risk increases even more. A person's cholesterol level is also affected by age, sex, heredity and diet. Cholesterol is vital for healthy cells. It is so important that the body does not rely on a dietary source, it makes its own. However, if the body accumulates too much cholesterol, it will deposit on the walls of arteries, which become damaged and may become blocked. If this happens, a heart attack could result. Excess cholesterol is produced when the diet is rich in saturated fats.

It is useful to study mechanisms of CHD and novel therapies to treat CHD. Animal models are particularly advantageous for studying the progression and presentation of diseases and offer a tremendous opportunity to test the efficacy of potential therapeutics and treatments. An ideal animal model for CHD would have features of the progression and incidence of CHD. It would be truly advantageous to have an animal model where heart attacks could be easily and reliably induced.

It is therefore an object of the present invention to produce an animal model for CHD where heart attacks can be reliably induced by altering the animal's diet.

It is a further object of the present invention to use the inducible heart attack model of heart disease to study the progression of CHD and test the effects of potential drugs and therapies.

BRIEF SUMMARY OF THE INVENTION

An animal model of coronary heart disease has been developed where myocardial infarct can be induced by altering the animal's diet. In all embodiments, this animal model is a result of reduced activity of scavenger receptor class BI (SR-BI) and apolipoprotein E (ApoE). In a preferred embodiment, the model is a result of crossbreeding two transgenic mouse lines: a knockout of SR-BI (SR-BI-/-) and an impaired ApoE expressor (hypoE). The animal is also referred to as a SR-BI KO/ApoER61$^{h/h}$. The impaired ApoE gene results in only 2-5% expression of ApoE and a reduction in cholesterol homeostasis. Resulting animals are predisposed to hypercholesterolemia but can live longer than a year on a normal low fat diet. Serum plasma levels can be significantly elevated by changing the animal's diet to one containing high levels of fat and cholesterol. Within a month on a high fat, high cholesterol diet, animals develop atherosclerosis and myocardial infarction occurs. Survival depends on the nature of the diet and the conditions of animal husbandry and can typically be around 20-30 days after administration of the modified diet depending on the specific conditions. This model is useful for studying the mechanisms of CHD and assaying for novel compounds to treating or preventing CHD. Surprisingly, survival rates of these animals is dependent on social interactions, with significantly earlier deaths for animals housed alone instead of in groups.

In another embodiment, triple knock out animals or double knockout (SR-BI -/- RAG -/-) hypoE animals are used for further analysis. Analysis of B- and T-cell deficient SR-BI/ApoE/RAG2 triple knockout mice established that B- and T-lymphocytes do not play a key role in the pathophysiology of this model of human disease.

This animal model can be used to study mechanisms and progression of CHD as a function of diet, treatment with drugs to be screened for efficacy or undesirable side effects, and social environmental effects. The studies described herein demonstrate that animals, which are deficient in SR-BI and hypomorphic for ApoE, are not only excellent models for atherosclerosis but also myocardial infarction and stroke, since the animals develop progressive heart block and coronary artery occlusions characterized by plaques resembling those in heart attack patients. The RAG tKO mice are particularly useful for screening of proteins or peptides in disease since there is no immune reaction to the proteins or peptides in these animals.

The finding regarding the effect of isolation on survival in the SR-BI knockout hypoApo E animals makes these animals the first animal model for social effects on chronic heart disease.

-▲- 3 weeks; -■- 2 months; -●- 6 months. A 50% survival rate was observed at approximately 30 days with no subject surviving longer than between 38 and 48 days depending on age.

Figure 4:
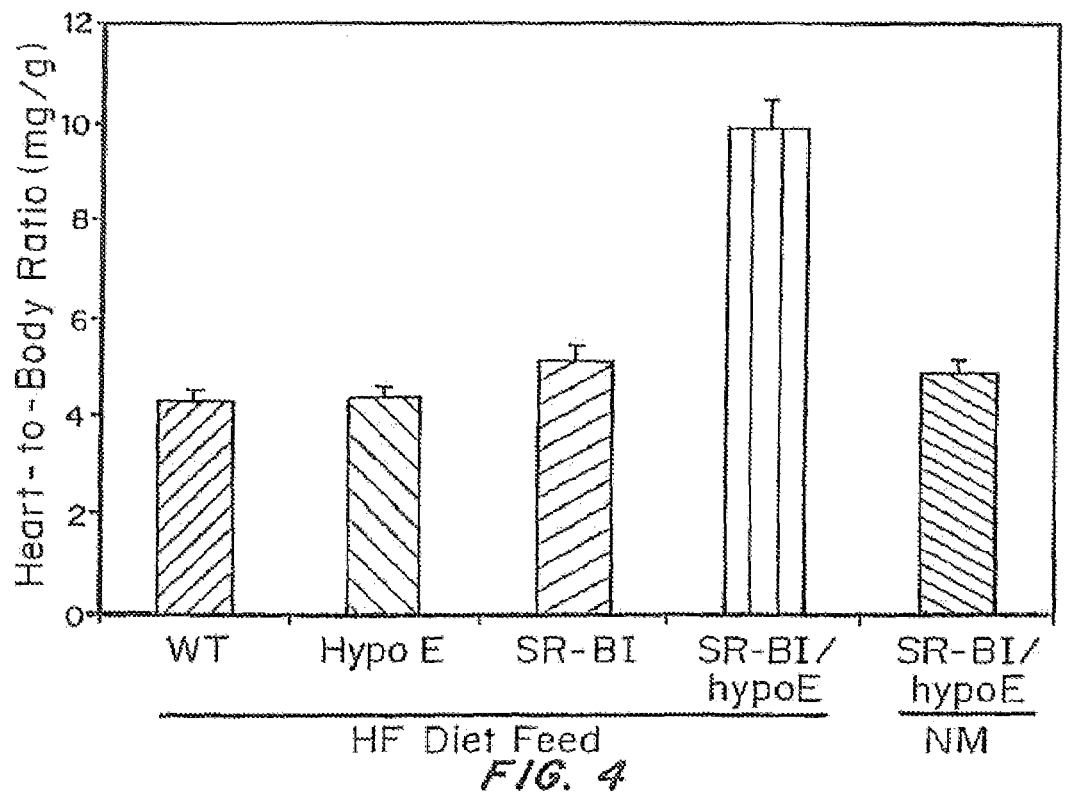

FIG. 4 is a bar graph depicting heart-to-body ratio (HBR) as a measure of heart weight. Wild type, hypoE and SR-BI mice all exhibited a HBR of around 4 mg/g when fed a high fat diet while the SR-BI/hypoE mouse exhibited a HBR of around 10 mg/g. SR-BI/hypoE mice on a normal diet maintained an HBR around 4-5 mg/g.

Figure 5:
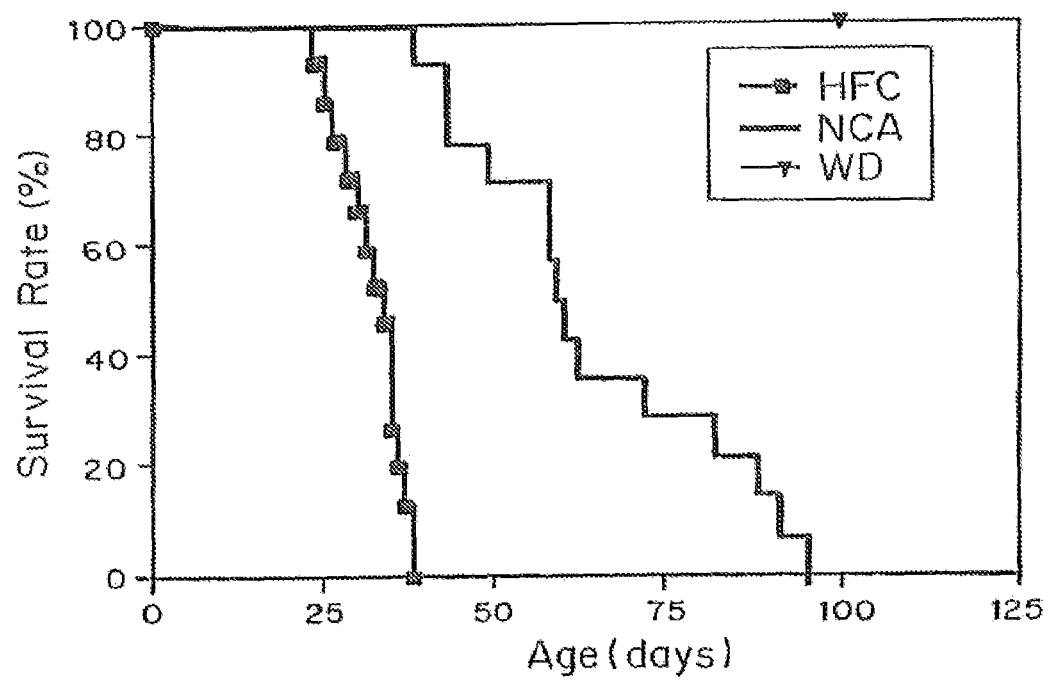

FIG. 5 is a survival curve showing the effects of the high fat (HF) diet (-■-), the NCA diet (NCA diet (-●-), and the Western Diet (WD) diet (-▼-) on survival for SR-BI/hypoE mice. SR-BI/hypo E mice were fed a normal low fat chow diet, a high fat (HF) diet consisting of 7.5% cocoa butter, 15.8% fat, 1.25% cholesterol, and 0.5% sodium cholate, a NCA diet consisting of 7.5% cocoa butter, 15.8% fat, and 1.25% cholesterol, or a Western Diet (WD) diet consisting of 21.2% fat, and 0.2% total cholesterol. A 50% survival rate was observed at approximately 30 days for the high fat diet and approximately 60 days for the NCA diet.

Figure 6:
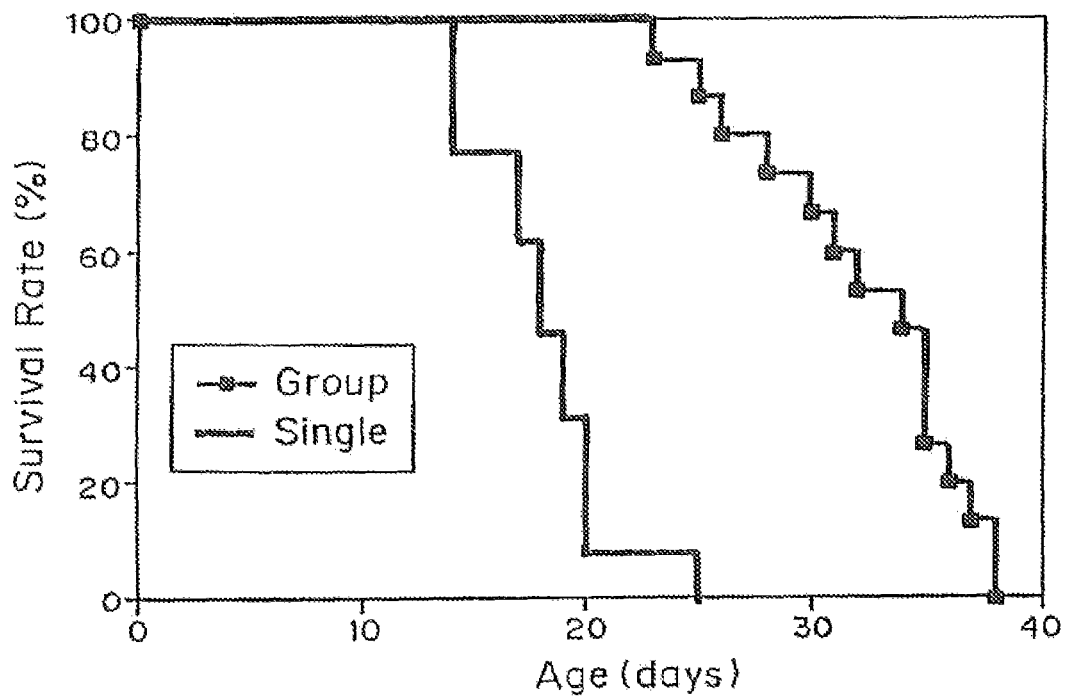

FIG. 6 is a survival curve showing the effects of the high fat (HF) diet for SR-BI/hypoE mice housed alone (-●-) or as a group (-■-). A 50% survival rate was observed at approximately 19 days for mice housed alone and approximately 30 days for mice housed as a group.

Figure 7:
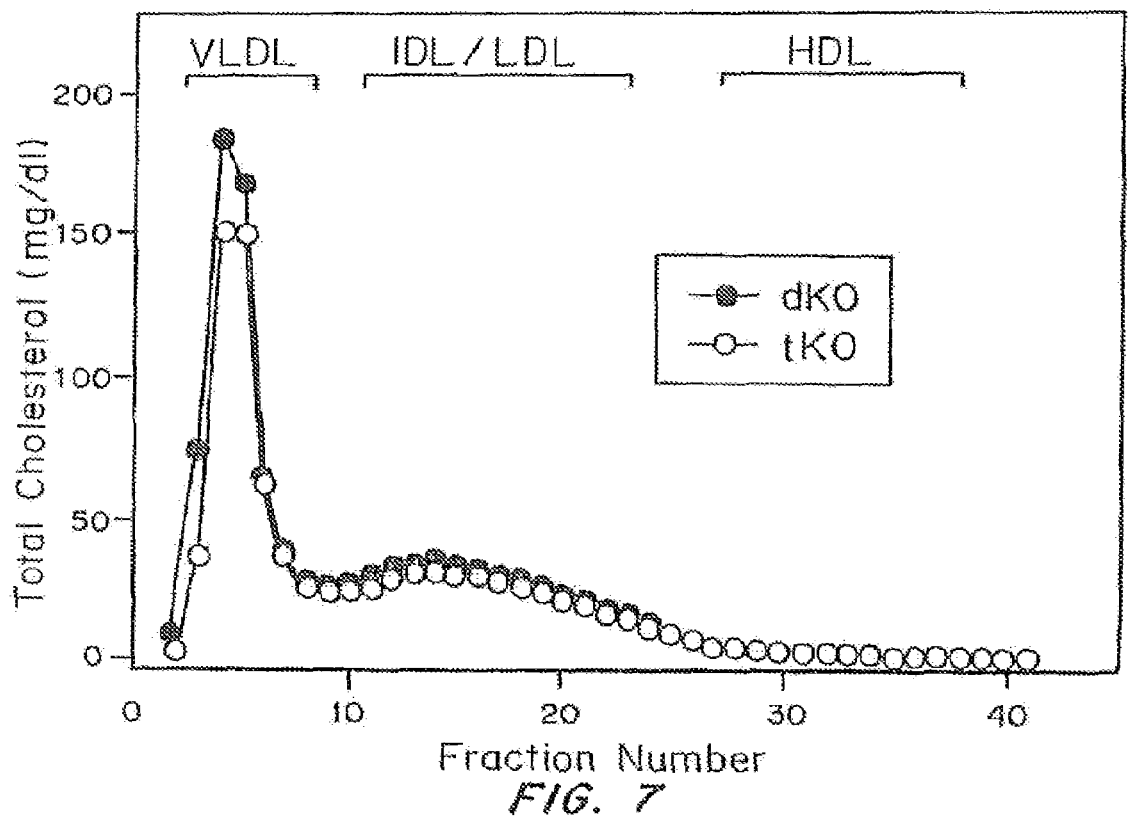

FIG. 7 is a graph of the Lipoprotein cholesterol profiles from SR-BI ApoE dKO (filled circles) and SR-BI/ApoE/RAG2 tKO (open circles) mice. Plasma lipoproteins from 39 day-old dKO and tKO mice were size fractionated (Superose 6-FPLC) and total cholesterol in each fraction (mg/dl plasma) determined. Chromatograms are representative of multiple, independent determinations.

Figure 8:
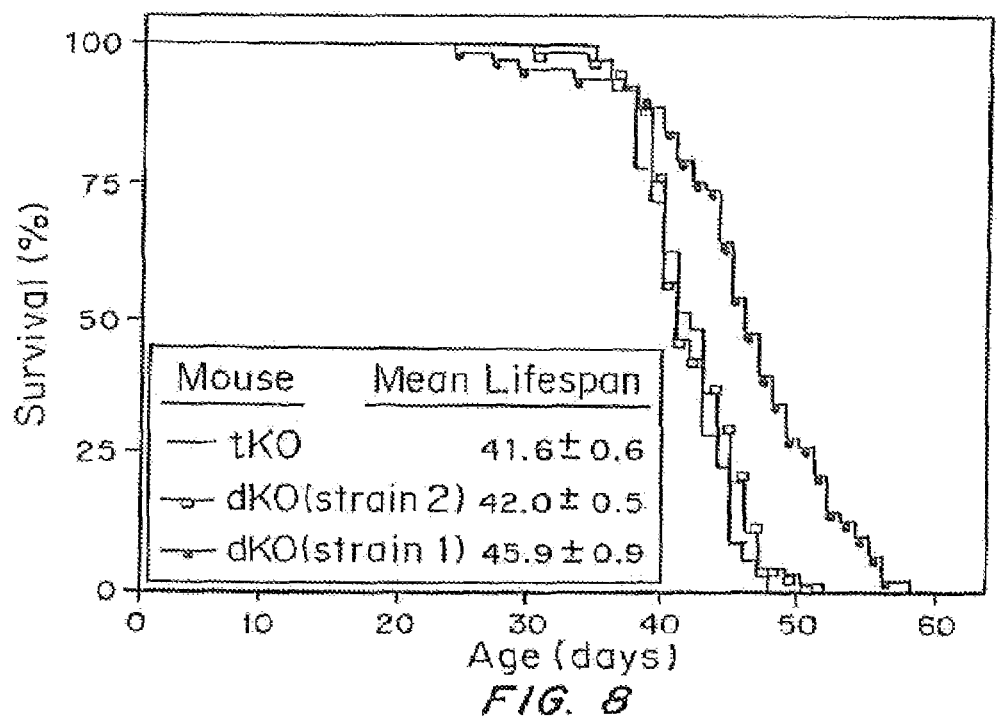

FIG. 8 is a graph of the effect of RAG2 deficiency and genetic background variation on survival of dKO mice. Survival curves from tKO (red line, mixed C57BL/6xSV129xBALB/c background, n=35), dKO (strain 2) (black line, C57BL/6xSV129xBALB/c background, n=65) and dKO (strain 1) (blue line, 75:25 C57BL/6:SV129 background, n=61) mice.

DETAILED DESCRIPTION OF THE INVENTION

The Animal Model

The preferred animal model for inducing heart attack by feeding a high fat diet is an animal with reduced activity of both SR-BI and ApoE. Preferably this animal model is a combination SR-BI knockout and hypoE mouse (SR-BI/hypoE). The SR-BI/hypoE mouse is defined as a transgenic mouse where the SR-BI gene is knocked out and the ApoE gene is inhibited to very low levels (~2-5%). Other embodiments include using animals where SR-BI activity is inhibited by other methods and crossing with animals where ApoE activity is reduced by other methods.

SR-BI can be inhibited by small molecules such as BLTs (Nielands et al. 2002 Proc Natl Acad Sci USA. 99(24):15422-7) or by expressing an inhibitory transgene such as siRNA which is commonly used to inhibit gene expression (See Dorsett Y, Tuschl T. 2004 *Nat Rev Drug Discov.* April 3(4): 318-29) or altering other genes that regulate SR-BI expression and activity such as PDZK1 (Kocher et al. 2003 *J Biol Chem* 278(52):52820-52825). Similarly, ApoE can be inhibited by siRNA and by small molecules and altering the expression of genes that regulate ApoE expression. Animals with reduced SR-BI activity can be crossed with animals with reduced ApoE activity to give a feeding-dependent CHD. Other combinations can include PDZK1 knockout mice crossed with ApoE knockout mice or hypoE mice. Transgenic mice are available with each single altered gene and a combination transgenic can be obtained by crossbreeding the two lines. Resulting combination transgenic mice should have characteristics of both single transgenics.

This model can be developed in other species that normally express SR-BI and ApoE using the general methods listed above to inhibit expression of appropriate SR-BI and ApoE species homologs. Examples of other species include but are not limited to non-human primates, rats, hamsters, rabbits, dogs, cats, cows, pigs, goats, and sheep. Improved methods of genetic manipulation have also facilitated the generation of transgenic livestock. (See Clark and Whitelaw 2003 *Nat Rev Genet.* October 4(10):825-33)

SR-BI Knockout Animals

Scavenger receptor class B, type I (SR-BI) is a receptor for high-density lipoprotein (HDL) that mediates cellular uptake of HDL cholesteryl ester (HDL CE) and cholesterol efflux and is the major route for cholesterol delivery to the steroidogenic pathway. SR-BI is a cell surface receptor for HDL and other lipoproteins (LDL and VLDL) and mediates the selective uptake of lipoprotein cholesterol by cells. SR-BI is localized in some cells in specialized microvillar channels in the plasma membrane that retain HDL and are sites of selective uptake of HDL CE. The formation of microvillar channels in the adrenal gland requires SR-BI and is regulated by adrenocorticotropin hormone. SR-BI-mediated uptake of HDL CE is a two-step process that requires high-affinity binding of HDL followed by transfer of CE to the membrane. CE uptake is followed by hydrolysis to free cholesterol by a neutral CE hydrolase. Studies of genetically manipulated strains of mice have established that SR-BI plays a key role in regulating lipoprotein metabolism and cholesterol transport to steroidogenic tissues and to the liver for biliary secretion. SR-BI knockout mice display elevated levels of plasma lipoprotein cholesterol.

In one embodiment, SR-BI knockout mice were made using po12sneobpA and herpes simplex virus thymidine kinase (TK) cassettes in coding exon 1. Methods for producing this animal are described in U.S. Patent Application Publication No. US2002/0108131 to Krieger et al. These animals exhibit hypercholesterolemia (Rigotti et al (1997) *Proc Natl Acad Sci* USA 94, 12610-12615) with abnormally low biliary cholesterol excretion. These animals do not exhibit rapid spontaneous atherosclerosis on a standard low fat chow diet and have been reported to have a high unesterified cholesterol/total cholesterol (UC/TC) ratio (~0.5) (Van Eck et al (2003) *J Biol Chem* 278(26): 23699-23705; Braun et al (2003) *Proc Natl Acad Sci* 100:7283-7288).

HypoE Animals

Apolipoprotein E (ApoE) is an important structural and functional protein component of lipoproteins that plays a prominent role in lipid metabolism. As a high affinity ligand for the LDL receptor, ApoE mediates the uptake of plasma remnant lipoproteins by the liver (Mahley and Ji (1999) *J Lipid Res* 40:1-16; Cooper (1997) *J Lipid Res* 38:2173-2192). In humans, three common types of ApoE exist: ApoE2, ApoE3 and ApoE4 (Weisgraber (1994) *Adv Protein Chem* 45:249-302). Subtype ApoE4 in humans is characterized by arginine at positions 112 and 158 and the murine ApoE4 analog is characterized by an arginine at position 61 in the protein sequence and is associated with elevated plasma cholesterol and LDL levels and predisposes to cardiovascular disease (Raffai et al (2001) *Proc Natl Acad Sci* USA 98(20): 11587-11591). Unlike ApoE2 and ApoE3, ApoE4 associates preferentially with VLDL.

In one embodiment, a hypomorphic ApoE (hypoE) mice is made by incorporating into the genome an Arg-61 allelic variant of mouse ApoE designed to resemble human ApoE4 (Raffai et al (2001) *Proc. Natl. Acad. Sci. USA* 98(20):11587-

11591) Methods for producing this animal are described in U.S. Patent Application Publication No. US2002/0194628 to Weisgraber et al. These animals express only approximately 5% of normal ApoE mRNA levels in all tissues and ApoE mRNA is barely detectable in tissues with normally low ApoE levels. Inherent variations exist between mice strains and therefore normal ApoE levels are defined as the ApoE levels observed in the wild type mouse strain used to generate the corresponding hypoE expressor. Insertion of a neo cassette flanked by loxP sites in the third intron of ApoE reduced expression of the Arg-61 allelic variant in ApoE mice and resulted in plasma ApoE levels that were approximately 2-5% of normal. Unlike other reduced ApoE mice, hypoE mice had a near normal lipoprotein cholesterol profile when fed a typical low fat chow diet. Total cholesterol and triglyceride levels were slightly higher than wild type (98 versus 65 mg/dl and 49 versus 26 mg/dl respectively). Levels of HDL were similar to wild type and most of the lipoprotein increases were seen in VLDL, IDL and LDL fractions. HypoE mice were susceptible to high fat diet-induced hypercholesterolemia, which was fully reversed within 3 weeks after resumption of a chow diet (Raffai and Weisgraber (2002) *J. Biol Chem.* 277(13) 11064-11068).

The SR-BI/hypoE Combination Animals

SR-BI −/− and hypoE animals can be crossbred to yield a combination mouse with both altered genes (denoted SR-BI/hypoE). The resulting SR-BI/hypoE mouse has elevated ApoE expression after fasting for either 4 hours or overnight. The increase in ApoE expression is a result of the SR-BI knockout as ApoE levels are lower in wild type and hypoE mice. Plasma lipids are markedly increased in SR-BI/hypoE mice specifically with respect to very low density lipoprotein (VLDL). On the normal chow diet, SR-BI/hypoE mice can live longer than one year in contrast to SR-BI/ApoE double knockout mice (denoted SR-BI/ApoE) which have a much reduced life expectancy of approximately 6 weeks.

The SR-BI/hypoE animal offers several unique advantages over the existing SR-BI/ApoE double knockout animal models. A significant breakthrough is the ability to rapidly induce cardiac dysfunction in these animals by diet modification alone. The SR-BI/hypoE mice offer greater ease of colony management as they do not suffer from spontaneous MI and CHD as seen in the SR-BI/ApoE mice. Another advantage is the ability to slow the development of coronary atherosclerosis and study the pharmacological treatments to alleviate CHD. It is also possible to study various nutritional components of MI development and CHD. This could not have been predicted from the SR-BI/ApoE model. The SR-BI/hypoE animal offers a unique model to study coronary atherosclerosis regression and recovery from heart failure by diet modification or restored ApoE function.

Method of Making

Generation of Animals with Reduced SR-BI or ApoE Activity

SR-BI can be inhibited directly or indirectly by administering small molecules such as BLTs (compounds that block lipid transport)(Nielands et al. 2002 *Proc Natl Acad Sci* USA. 99(24): 15422-7) or other compounds or antibodies that may have blocking actions on SR-BI or proteins that regulate SR-BI activity. SR-BI activity can also be inhibited by expressing an inhibitory transgene such as siRNA which is commonly used to inhibit gene expression. (See Dorsett Y, Tuschl T. 2004 *Nat Rev Drug Discov*. April 3(4):318-29). Double-stranded RNA-mediated interference (RNAi) is a simple and rapid method of silencing gene expression in a range of organisms. The silencing of a gene is a consequence of degradation of RNA into short RNAs that activate ribonucleases to target homologous mRNA. The resulting phenotypes either are identical to those of genetic null mutants or resemble an allelic series of mutants. Similarly, ApoE can be inhibited by siRNA and by small molecules or antibodies in a similar manner. Altering the expression of genes that regulate ApoE expression is another method to reduce ApoE activity. Animals with reduced SR-BI activity can be crossed with animals with reduced ApoE activity to give a feeding-dependent CHD.

Generation of Transgenic Animals

With the knowledge of the sequence and or gene structure of the cDNA or genomic DNA encoding SR-BI, ApoE and regulatory sequences regulating expression thereof, it is possible to generate transgenic animals, especially rodents, with genotype of SR-BI$^{-/-}$/hypoE (SR-BI/hypoE). For example altering other genes that regulate SR-BI expression and activity such as PDZK1 (Kocher et al. 2003 *J Biol Chem* 278(52): 52820-52825) also can inhibit SR-BI activity. Transgenic mice are separately generated for each altered gene and can be crossbred to obtain combination genotypes.

The SR-BI knockout animals are preferably made using techniques that result in "knocking out" of the gene for SR-BI. These animals are preferably made using a construct that includes complementary nucleotide sequence to the SR-BI gene, but does not encode functional SR-BI, and is most preferably used with embryonic stem cells to create chimeras. Animals which are heterozygous for the defective gene can also be obtained by breeding a homozygote normal with an animal which is defective in production of SR-BI. Methods are disclosed in U.S. Patent Application Publication No. 2002/0108131 incorporated by reference herein.

HypoE mice expressing reduced levels of ApoE can be generated by homologous recombination in embryonic stem cells. (Raffai et al. (2001) *Proc Natl Acad Sci* U.S.A. 98, 11587-11591). A neo cassette flanked by loxP sites was inserted into ApoE intron 3 to follow the replacement of the human equivalent of Thr-61 by an arginine. (Raffai and Weisgraber (2002) J. Biol Chem. 277(13)11064-11068). Correctly targeted embryonic stem cell clones were injected into blastocysts using standard microinjection techniques.

These manipulations can performed by insertion of cDNA or genomic DNA into the embryo or embryonic stem cells using microinjection or other techniques known to those skilled in the art such as electroporation, as described below. Nuclear transfer techniques can also be used to transfer altered genetic material in generating transgenic animals. Alternatively SR-BI and ApoE encoding genes can be modified by homologous recombination with a DNA for a defective gene, such as one containing within the coding sequence an antibiotic marker, which can then be used for selection purposes.

Animal Sources

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats and can easily be extended to other species when analogous techniques are developed.

Microinjection Procedures

The procedures for manipulation of the embryo and for microinjection of DNA are described in detail in Hogan et al. Manipulating the mouse embryo, Cold Spring Harbor Laboratory, Cold Spring Harbor, N.Y. (1986), the teachings of which are incorporated herein. These techniques are readily applicable to embryos of other animal species, and, although the success rate is lower, it is considered to be a routine practice to those skilled in this art.

Transgenic Animals

Female animals are induced to superovulate using methodology adapted from the standard techniques used with mice, that is, with an injection of pregnant mare serum gonadotrophin (PMSG; Sigma) followed 48 hours later by an injection of human chorionic gonadotrophin (hCG; Sigma). Females are placed with males immediately after hCG injection. Approximately one day after hCG, the mated females are sacrificed and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5C incubator with a humidified atmosphere at 5% $CO_2$, 95% air until the time of injection.

Randomly cycling adult females are mated with vasectomized males to induce a false pregnancy, at the same time as donor females. At the time of embryo transfer, the recipient females are anesthetized and the oviducts are exposed by an incision through the body wall directly over the oviduct. The ovarian bursa is opened and the embryos to be transferred are inserted into the infundibulum. After the transfer, the incision is closed by suturing.

Embryonic Stem (ES) Cell Methods

Introduction of Exogenous DNA into ES Cells for Making Transgenic of Knockout Animals:

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E. J. Robertson, (IRL Press 1987), the teachings of which are incorporated herein. Although the preferred method of gene transfer is by homologous recombination (described below), older methods can still be used. Selection of the desired clone of transgene-containing ES cells is accomplished through one of several means. Transfection is carried out by one of several methods described in detail in *Current Protocols in Molecular Biology: Ch. 9 Introduction of DNA into Mammalian Cells*; John Wiley & Sons, New York, N.Y., ©2001). Calcium phosphate/DNA precipitation, direct injection, and electroporation are the preferred methods. In these procedures, a number of ES cells, for example, $0.5 \times 10^6$, are plated into tissue culture dishes and transfected with a mixture of the linearized nucleic acid construct containing the gene of interest. Colonies of cells resistant to G418 are isolated using cloning rings and expanded. DNA is extracted from drug resistant clones and Southern blotting experiments using the nucleic acid sequence as a probe are used to identify those clones carrying the desired nucleic acid sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, Nature 338, 150-153 (1989)). DNA introduction by electroporation is less efficient and requires a selection step.

Methods for positive selection of the recombination event (i.e., neo resistance) and dual positive-negative selection (i.e., neo resistance and ganciclovir resistance) and the subsequent identification of the desired clones by PCR have been described by Joyner et al., Nature 338, 153-156 (1989) and Capecchi, (1989), the teachings of which are incorporated herein. The target sequence can also be "floxed" using methods reviewed in Sauer (*Methods.* 1998 April ;14(4):381-92) for removal by crossing with an appropriate expresser of cre-recombinase.

Embryo Recovery and ES Cell Injection

Naturally cycling or superovulated females mated with males are used to harvest embryos for the injection of ES cells. Embryos of the appropriate age are recovered after successful mating. Embryos are flushed from the uterine horns of mated females and placed in Dulbecco's modified essential medium plus 10% calf serum for injection with ES cells. Approximately 10-20 ES cells are injected into blastocysts using a glass microneedle with an internal diameter of approximately 20 m.

Transfer of Embryos to Pseudopregnant Females

Randomly cycling adult females are paired with vasectomized males. Recipient females are mated such that they will be at 2.5 to 3.5 days post-mating (for mice, or later for larger animals) when required for implantation with blastocysts containing ES cells. At the time of embryo transfer, the recipient females are anesthetized. The ovaries are exposed by making an incision in the body wall directly over the oviduct and the ovary and uterus are externalized. A hole is made in the uterine horn with a needle through which the blastocysts are transferred. After the transfer, the ovary and uterus are pushed back into the body and the incision is closed by suturing. This procedure is repeated on the opposite side if additional transfers are to be made.

Identification of Transgenic Animals.

Samples (1-2 cm of mouse tails) are removed from young animals. For larger animals, blood or other tissue can be used. To test for chimeras in the homologous recombination experiments, i.e., to look for contribution of the targeted ES cells to the animals, coat color has been used in mice, although blood could be examined in larger animals. DNA is prepared and analyzed by both Southern blot and PCR to detect transgenic founder ($F_0$) animals and their progeny ($F_1$ and $F_2$).

Once the transgenic animals are identified, lines are established by conventional breeding. Dual species crosses can be obtained by cross mating and breeding to homozygosity. Methods of breeding transgenic mice are routine in the art.

Generation of Other Transgenic Animals

The SR-BI knockout and double knockouts can be crossed with other types of genetically modified animals (either naturally occurring mutations or genetically engineered animals). Many such animals are described in the literature and available from companies such as Jackson Laboratories, Bar Harbor, Me.

Method of Inducing CHD and MI in Animal Model

The SR-BI/hypoE mice have a life expectancy longer than a year when fed a normal low fat chow diet such as the RM3 diet containing 4.3% fat (Special diet services, Witham, UK). When fed a high fat, high cholesterol diet such as a Paigen or Paigen-type diet consisting of, for example, 7.5% cocoa butter, 15.8% fat, 1.25% cholesterol, and 0.5% sodium cholate, (ICN, Costa Mesa, Calif.; Research Diets, Inc., New Brunswick, N.J.), the mice develop severe hypercholesteremia. Such a diet causes atherosclerosis. SR-BI/hypoE mice lose weight after a high fat feeding. Between 20 and 30 days of feeding the high-fat diet, survival of the SR-BI/hypoE mice goes from 100% to 50%, ultimately reaching 0% by approximately 45 days. Longevity depends in part of the number of animals per cage with animals maintained at only one mouse per cage exhibiting shorter survival times. The SR-BI/hypoE mice display a dramatically increased heart weight compared to hypoE mice similarly fed a high-fat diet. Heart to body ratio measurements for wt, SR-BI or hypoE mice fed a high-fat diet are approximately 4 mg/g. The ratio for SR-BI/hypoE mice is approximately 10 mg/g.

The induction of MI in this animal model is dependent on the type of diet. Not all high-fat diets are effective in inducing MI. Feed mixes with high cholesterol and no cholic acid such as the classic Western Diet consisting of approximately 20% fat and 0.2% total cholesterol do not work well to induce a rapid onset of CHD in the SR-BI/hypoE mouse. Western Diets are available from Hope Farms, Woerden, The Netherlands, and Harlan Teklad, Madison, Wis.

Studying CHD

This animal model can be used to study mechanisms and progression of CHD as a function of diet, treatment with drugs to be screened for efficacy or undesirable side effects, and social environmental effects.

The studies described herein demonstrate that animals which are deficient in SR-BI and hypomorphic for ApoE are not only excellent models for atherosclerosis but also myocardial infarction and should be excellent animal models for stroke, since the animals develop progressive heart block and coronary artery occlusions characterized by plaques resembling those in heart attack patients. This animal can be induced with a high-fat, high cholesterol diet and then monitored at various time points until occurrence of heart attack. Animals can be studied using histology, electron microscopy, echocardiography, EKG, angiogram, and other diagnostic or imaging techniques. Differential gene expression during progression of CHD can be studied using DNA microarrays, differential display PCR or kinetic (real-time) PCR to identify candidate gene targets that change during onset of CHD. Proteomics and metabolomics can be used to assay for markers of disease in the blood, urine and other accessible tissues.

Assaying for Compounds Affecting Behavioral Factors

The deleterious effects on health of social isolation have been recognized for decades. Social isolation increases mortality and morbidity in the general human population and in individuals with established morbidity, especially CHD. Atherosclerosis is reportedly higher in single-caged female monkeys than their socially housed counterparts, perhaps due to altered autonomic activity (higher heart rates). In mice, social isolation can decrease body weight gain, and food consumption, and increase stereotypic and vertical movements (locomotor activity), basal corticosterone levels and aggressiveness in a novel environment relative to group-housed animals. Social isolation by individual housing not only involves potential alteration in psychosocial activity, but also can be associated with decreased complexity of the environment, loss of tactile stimulation, and increased metabolic demands of temperature maintenance and possible alteration in sympathetic tone.

Although no apparent differences in the survival of dKO mice housed singly or in groups has been observed, a profound reduction in longevity of HFC-fed SR-BI KO/ApoER61$^{h/h}$ mice when housed singly (n=13 or 15) was observed as demonstrated in the following examples. It is not clear if this effect is a consequence of altered food or water intake, altered basal metabolic rates, altered levels of stress (all of which are readily measured), or more complex phenomena. Preliminary studies on small numbers of animals (n=3 or 4) have shown no significant difference in the plasma total cholesterol levels or FPLC lipoprotein cholesterol profiles at 7 and 14 days of HFC-feeding for singly or group housed animals, raising the possibility that ingestion and absorption of dietary fats, and plasma lipoproteins levels may not be substantially different. Mechanisms that resemble those involved with the effects of human social isolation may contribute to this effect. Thus, the SR-BI KO/ApoER61$^{h/h}$ mice are useful for studying the mechanisms underlying the relationships between social isolation and CHD. As demonstrated in the following examples, the dKO survival is a function not just of diet but also social effects, with animals in isolation having significantly shorter lives when fed high fat diets. This provides an animal model for testing drugs such as Prozac for their effect on survival in patients with CHD.

Assaying for Therapeutics or Undesirable Side Effects

Compounds which prevent or alter progression of disease can be screened using this animal model as well as molecules that lower high cholesterol. The compound can be administered before, during or after the animal is fed a lipid enriched (high fat) diet. Symptoms of CHD progression can be monitored using diagnostic tests known in the art. Similarly, markers for CHD progression can be monitored by assaying blood, urine or any accessible fluid. Possible compounds to be screened include synthetic or organic small molecules, proteins, peptides, oligonucleotides, and gene drugs such as siRNA or nutraceuticals. Compounds can be administered singly or in combination with each other. The animal model can also be used to screen for which type of diet in combination with a compound is effective in preventing or altering progression of the disease.

The SR-BI/ApoE/RAG2 tKO or SR-BI/RAG2 dKO hypoE mice are particularly useful for screening of proteins or peptides in disease since there is no immune reaction to the proteins or peptides in these animals.

Compounds are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compounds may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287-341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

The present invention will be further understood by reference to the following non-limiting examples.

EXAMPLE 1

Production and Characterization of Combination Transgenic Animals which do not Express SR-BI and have Reduced ApoE Expression (hypoE)

Generation of SR-BI/hypoE mutant mice.

SR-BI/hypoE mice were generated by crossbreeding established SR-BI knockout mice with hypoE mice. Homozygous SR-BI knockout dams are infertile (Miettinen et al. (2001) *J Clin Invest.* 108(11):1717-22; Rigotti et al (2003) *Endocr Rev.* 24(3):357-87). It is therefore necessary to use an SR-BI knockout male crossing with a hypoE dam while also accounting for the infertility of female mice during crossbreeding. Alternatively, the cholesterol lowering drug probucol has been shown to restore fertility in the SR-BI knockout females and may be administered during the breeding protocol (Miettinen et al. 2001).

Characterization of Plasma Lipids and Apolipoproteins

Figure 1:
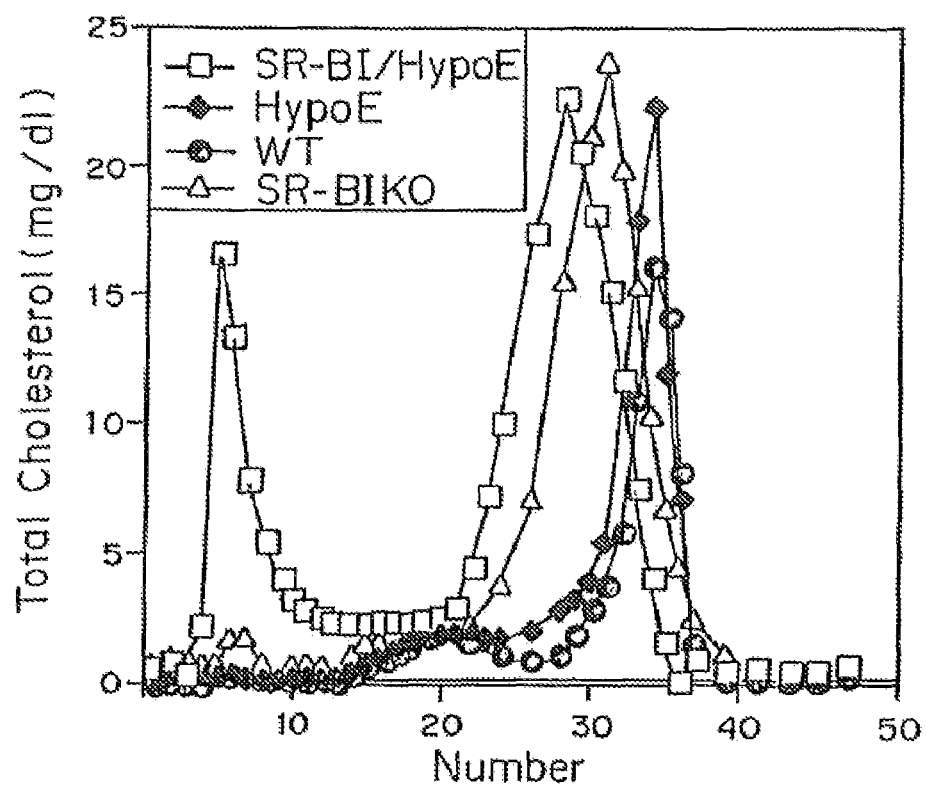
FIG. 1 is a line plot showing the plasma lipid profile for the different transgenic mice fed a normal diet with low cholesterol. The different animals are denoted as follows: -●- wild type; -Δ- SR-BI -/-; -◆-hypoE; -□- SR-BI/hypo E. There is a substantial increase in VLDL sized lipoproteins in the SR-BI/hypoE mice compared to wild type or single transgenic mice alone.

Plasma lipids and apolipoproteins were assayed for wild type and SR-BI/hypoE mice and compared with hypoE, SR-BI-/- and ApoE-/- single knockout mice when fed a normal low fat, low cholesterol diet. These data are summarized in Table 1 and shown in FIG. 1.

TABLE 1

Plasma lipids and apolipoprotein comparison on normal diet (mg/dl)

|  | TC | FC | PL | TG | Ratio FC/TC | HDL |
|---|---|---|---|---|---|---|
| WT (n = 5) | 81 ± 31 | 19 ± 9 | 127 ± 40 | 40 ± 11 | 0.23 ± 0.04 | 52 ± 19 |
| SR-BI -/- (n = 6) | 189 ± 46 | 92 ± 23 | 161 ± 34 | 38 ± 8 | 0.49 ± 0.02 | 125 ± 29 |
| hypoE (n = 4) | 124 ± 16 | 30 ± 4 | 160 ± 38 | 36 ± 20 | 0.24 ± 0.02 | 83 ± 15 |
| ApoE -/- (n = 8) | 450 ± 63 | 147 ± 20 | 236 ± 19 | 48 ± 15 | 0.33 ± 0.04 | 33 ± 10 |
| SR-BI/hypoE (n = 9) | 282 ± 25 | 173 ± 19 | 200 ± 17 | 47 ± 9 | 0.61 ± 0.06 | 148 ± 18 |

Figure 2:
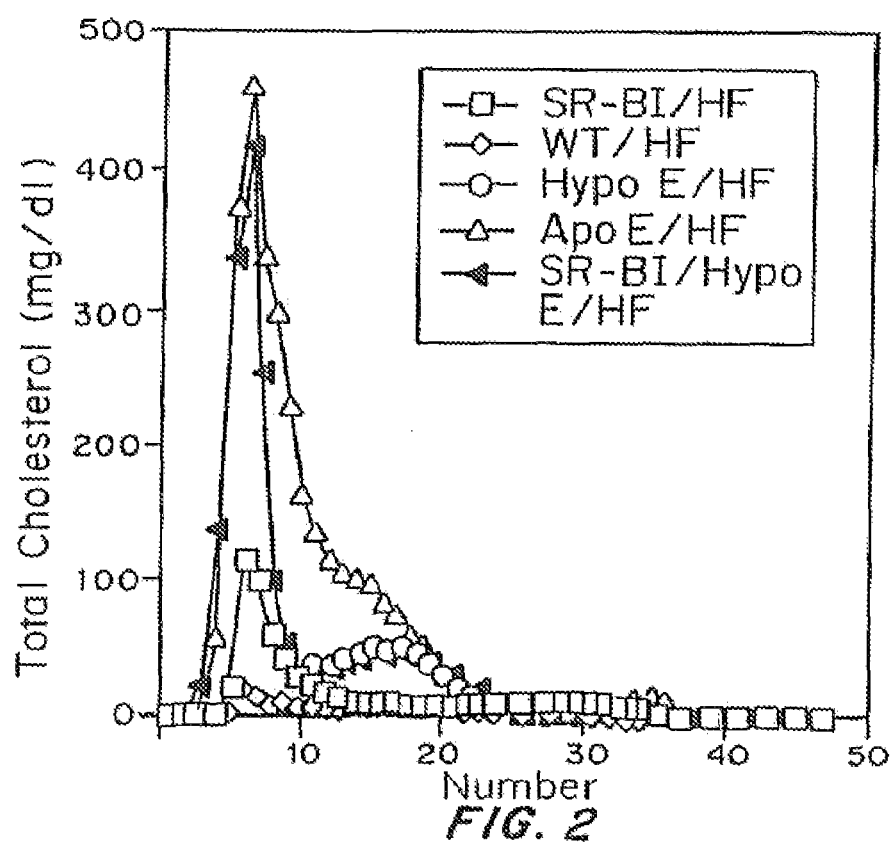
FIG. 2 is a line plot showing the plasma lipid profile for the different transgenic mice fed a high fat diet. The different animals are denoted as follows: -◇- wild type; -□- SR-BI -/-; -Δ- ApoE -/-; -○- hypoE; -◀- SR-BI/hypo E. There is a substantial increase in VLDL sized lipoproteins in the ApoE-/- and SR-BI-hypoE mice compared to the other transgenic mice tested.

Abbreviations used:
TC—Total cholesterol;
FC—Free Cholesterol;
PL—phospholipids;
TG—triglycerides;
HDL—high density lipoprotein, cholesteryl esters Animals were fed a high fat, high cholesterol, Paigen-type diet and plasma lipids and lipoproteins were similarly assayed. These results are summarized in Table 2 and shown in FIG. 2.

TABLE 2

Plasma lipids and apolipoprotein comparison on high fat diet

|  | TC | FC | PL | TG | Ratio FC/TC | HDL |
|---|---|---|---|---|---|---|
| WT(n = 10) | 214 ± 43 | 51 ± 12 | 168 ± 41 | 14 ± 7 | 0.24 ± 0.03 | 95 ± 21 |
| SR-BI -/- (n = 5) | 693 ± 120 | 453 ± 75 | 408 ± 76 | 41 ± 10.5 | 0.65 ± 0.03 | 189 ± 52 |
| hypoE (n = 8) | 1214 ± 224 | 277 ± 35 | 421 ± 41 | 34 ± 13 | 0.23 ± 0.04 | 18 ± 6 |
| ApoE -/- (n = 10) | 2731 ± 681 | 902 ± 325 | 857 ± 215 | 34 ± 8 | 0.32 ± 0.04 | 18 ± 6 |
| SR-BI/ApoE -/- | 970 ± 83 | 781 ± 65 | 678 ± 96 | 53 ± 16 | 0.806 ± 0.007 |  |
| SR-BI/hypoE (n = 6) | 1630 ± 337 | 1284 ± 274 | 976 ± 253 | 72 ± 13 | 0.79 ± 0.04 | 226 ± 36 |

Body weight was assessed in the various transgenic mice on normal and high fat Paigen-type diet. The SR-BI/hypoE mouse was the only mouse that lost weight on the high fat diet. These data are summarized in Table 3.

TABLE 3

Body weight of transgenic mice strains

| Age | Wild Type | hypoE | SR-BI -/- | SR-BI/hypoE |
|---|---|---|---|---|
| 25 days | 13.0 g | 13.0 g | 13.3 g | 13.3 g |
| 60 days | 21.9 g | 22.3 g | 24.1 g | 23.0 g |
| 60 days (high fat for 28 days) | 24.7 g | 26.3 g | 27.5 g | 19.8 g |

Figure 3:
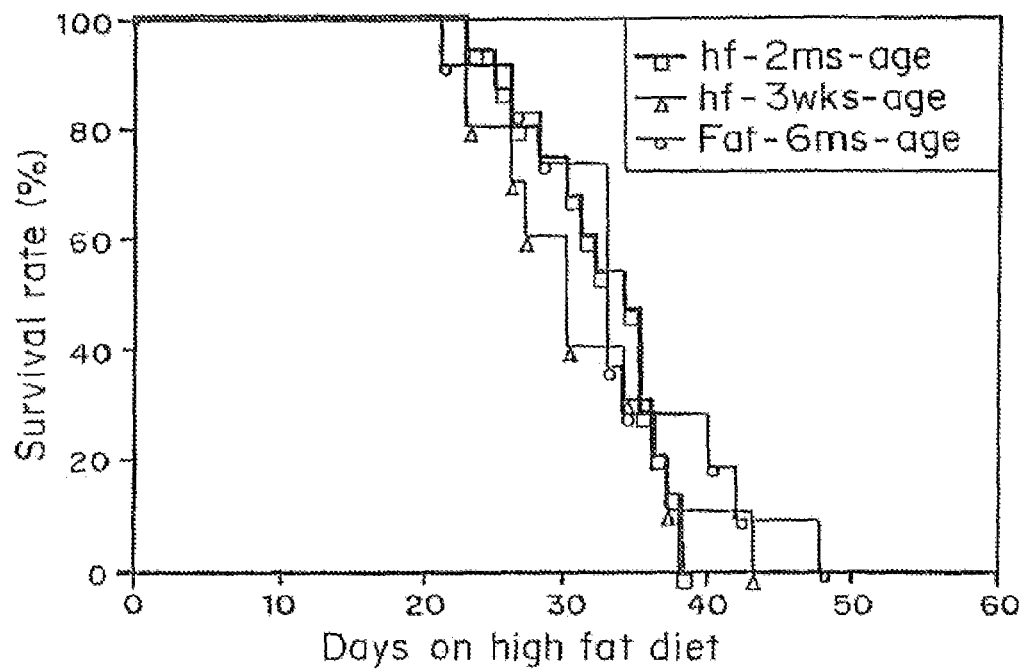
FIG. 3 is a survival curve showing the effects of the high fat diet (7.5% cocoa butter, 15.8% fat, 1.25% cholesterol, 0.5% sodium cholate) on survival for mice where feeding of the high fat diet began at three different ages. The different ages are denoted as follows.

Survival was assessed after the animals were administered a high-fat Paigen-type diet consisting of 7.5% cocoa butter, 15.8% fat, 1.25% cholesterol and 0.5% sodium cholate. Animals of various ages (3 weeks, 2 months and 6 months) were fed the high-fat diet and monitored for survival. For all age groups, mean survival time was approximately 30days after commencement of the high-fat diet. This is shown in FIG. 3.

Heart weight was assessed for wild type, hypoE, SR-BI-/- and SR-BI/hypoE mice after being fed the high-fat diet. FIG. 4 is a bar graph depicting heart-to-body ratio (HBR) as a measure of heart weight. Wild type, hypoE and SR-BI mice all exhibited a HBR of around 4 mg/g when fed a high fat diet while the SR-BI/hypoE mouse exhibited a HBR of around 10 mg/g. SR-BI/hypoE mice on a normal diet maintained an HBR around 4-5 mg/g.

Cardiac function was assessed in wild type, hypoE, SR-BI-/- and SR-BI/hypoE mice after being fed the high-fat diet using electrocardiography and echocardiography. Normal electrocardiography (ECG) patterns were seen in wild type, hypoE, and SR-BI−/− mice while cardiac dysfunction was observed in SR-BI/hypoE mice. Analysis using echocardiography, showed that SR-BI/hypoE mice displayed increased heart wall thickness, increased LV (left ventricular) internal dimension at end systole (LVIDES), and reduced fractional shortening indicating contractile dysfunction. These data are summarized in Table 4. The electrocardiography and echocardiography results demonstrate that SR-BI/hypoE mice fed a high-fat diet have impaired heart function.

TABLE 4

Echocardiographic analysis of mice on a high-fat diet which do not express SR-BI and have reduced ApoE expression (hypoE).

|  | SR-BI/hypoE normal diet (n = 6) | hypoE high-fat diet (n = 6) | SR-BI/hypoE high-fat diet (n = 9) |
| --- | --- | --- | --- |
| Heart Rate (bpm*) | 550 ± 23 | 539 ± 47 | 425 ± 27 |
| LVIDED (cm) | 0.31 ± 0.02 | 0.32 ± 0.01 | 0.32 ± 0.01 |
| LVIDES (cm) | 51 ± 2.3 | 59 ± 4.4 | 36 ± 2.3 |
| FS (%) | 51 ± 2.3 | 50 ± 4.4 | 36 ± 2.3 |
| PWT (cm) | 0.103 ± 0.005 | 0.102 ± 0.006 | 0.129 ± 0.009 |
| LV mass D3 (g) | 0.115 ± 0.008 | 0.115 ± 0.011 | 0.161 ± 0.017 |

*Values are mean ± SE.
Abbreviations used:
bpm, beats per minute;
LVIDED, left ventricular internal dimension (end diastole);
LVIDES, left ventricular internal dimension (end systole);
FS, fraction shortening;
PWT, posterior wall thickness;
LV mass, left ventricular mass.

EXAMPLE 2

Manipulation of the Progress of CHD by Feeding Mice Which do not Express SR-BI and Have Reduced ApoE Expression (hypoE) Different High Fat Diets SR-BI/hypo E mice were generated as described in Example 1. SR-BI/hypo E mice were fed a normal low fat chow diet, a high fat (HF) diet consisting of 7.5% cocoa butter, 15.8% fat, 1.25% cholesterol, and 0.5% sodium cholate, a NCA diet consisting of 7.5% cocoa butter, 15.8% fat, and 1.25% cholesterol, or a Western Diet (WD) diet consisting of 21.2% fat, and 0.2% total cholesterol.

Plasma lipids and apolipoproteins were assayed for SR-BI/hypoE mice when fed a normal low fat, low cholesterol diet, the HF diet, the NCA diet, or the WD diet. These data are summarized in Table 5.

Survival was assessed after the animals were administered a normal diet, a HF diet, a NCA diet, or a WD diet. Animals were fed the various diets and monitored for survival. Animals on the HF diet and the NCA diet died within seven weeks and fifteen weeks, respectively. Animals on the WD diet were not affected at 100 days. A 50% survival rate was observed at approximately 30 days for the high fat diet and approximately 60 days for the NCA diet. This is shown in FIG. 5.

EXAMPLE 3

Survival of Mice Which do not Express SR-BI and Have Reduced ApoE Expression (hypoE) Depends on the Number of Animals Per Cage SR-BI/hypo E mice were generated as described in Example 1. SR-BI/hypo E mice were fed a high fat (HF) diet consisting of 7.5% cocoa butter, 15.8% fat, 1.25% cholesterol, and 0.5% sodium cholate.

SR-BI/hypo E mice were housed as a group or single and survival was assessed after the animals were administered a HF diet. Animals were fed the normal or HF diet and monitored for survival. SR-BI/hypoE mice housed alone exhibit shorter survival times than mice housed as a group. Animals on the HF diet housed alone died within four weeks while animals on the HF diet housed as a group died within seven weeks. A 50% survival rate was observed at approximately 19 days for animals housed alone and approximately 30 days for animals housed as a group. This is shown in FIG. 6.

After 14 days on the HF diet, SR-BI/hypo E mice housed alone displayed elevated levels of cholesterol as compared to SR-BI/hypo E mice housed as a group. Total cholesterol (TC) was assayed for SR-BI/hypoE mice housed as a group or single when fed the HF diet. These data are summarized in Table 6.

TABLE 6

Total cholesterol level of SR-BI/hypoE mice housed as a group or single on the HF diet

| Day | TC Group (n = 4) | TC Single (n = 3) |
| --- | --- | --- |
| 0 days | 303 ± 38 | 306 ± 58 |
| 7 days | 1262 ± 327 | 1354 ± 203 |
| 14 days | 1531 ± 498 | 1935 ± 840 |

TABLE 5

Plasma lipid and apolipoprotein levels of SR-BI/hypo E mice on different high fat diets.

| Diet | TC | UC | PL | TG | Ratio UC/TC | UC + PL |
| --- | --- | --- | --- | --- | --- | --- |
| Normal (n = 19) | 1010 ± 237 | 817 ± 188 | 686 ± 93 | 42 ± 18 | 0.811 ± 0.032 | 6.63 ± 1.7 |
| HF diet (n = 1) | 6630 ± 337 | 1284 ± 274 | 976 ± 253 | 72 ± 13 | 0.787 ± 0.045 | 5.58 ± 1.5 |
| NCA diet (n = 14) | 918 ± 192 | 692 ± 168 | 608 ± 156 | 45 ± 24 | 0.751 ± 0.057 | 4.98 ± 1.4 |
| WD diet (n = 18) | 703 ± 131 | 496 ± 144 | 525 ± 145 | 61 ± 29 | 0.697 ± 0.104 | 4.22 ± 1.9 |

Abbreviations used:
TC—Total cholesterol;
UC—Unesterified Cholesterol;
PL—phospholipids;
TG—triglycerides.

EXAMPLE 4

Lymphocytes are Present in the Hearts of SR-BI(−/−)/ApoE(−/−) Mice

Generation of SR-BI (−/−)/ApoE (−/−) mice.

Mice (mixed C57BL/6x129 background) were housed and fed a normal chow diet as described in Rigotti A., et al., (1997). SR-BI$^{-/-}$ mice (Rigotti A., (1997)), and ApoE$^{-/-}$ mice (The Jackson Laboratory, Zhang, S. H., et al., (1992), and Zhang, S. H., et al., (1994)), were mated and the double heterozygous offspring were intercrossed. The resulting SR-BI$^{+/-}$ApoE$^{-/-}$ offspring were mated to produce single ApoE KO and double SR-BI/ApoE KO animals. Genotypes were determined by PCR analysis (Rigotti A., et al., (1997)).

Presence of Lymphocytes in the Hearts of SR-BI(−/−)/ApoE(−/−) Mice

At 5-6 weeks of age, the hearts of double knockout (dKO) mice exhibit extensive fibrosis around the ventricular outflow tract and patchy myocardial infarctions (MIs) in the apex, right ventricular wall and interventricular septum. However, the role of B-or T-lymphocytes in coronary heart disease (CHD) in SR-BI(−/−)/ApoE(−/−) mice has not been directly examined. Clusters of cells that tended to coincide with regions of immune-infiltrated and damaged tissue stained with antibodies against the T-cell marker CD4, but not with isotype control antibodies, raising the possibility that T-lymphocytes might contribute to myocardial injury. The pan B-cell marker, anti-CD19, did not stain heart sections, indicating these cells were absent.

EXAMPLE 5

The Role of Lymphocytes in the Cardiac Pathophysiology of Mice that do not Express SR-BI(−/−) and ApoE(−/−)

Triple knockout mice were generated to further examine the role of lymphocytes in the pathology. RAG2(−/−) do not produce lymphocytes and are severely immunodeficient.

Generation of SR-BI (−/−)/ApoE (−/−)/RAG2 (−/−) Mice

SR-BI (−/−)/ApoE (−/−)/RAG2 (−/−) triple knockout (tKO) mice and control SR-BI (−/−)/ApoE (−/−)/RAG2 (+/+) double knockout (dKO, strain 2) mice were generated by crossing SR-BI(+/−)ApoE(−/−) females (75:25 C57BL/6: SV129 background, strain 1)1 with SR-BI(−/−)/RAG2(−/−) males (mixed C57BL/6xSV129xBALB/c background)27. The offspring SR-BI(+/−)/ApoE(+/−)/RAG2(+/−) females were then crossed to sibling SR-BI(−/−)/ApoE(+/−)/RAG2 (+/−)males to generate littermate isolates of tKO and dKO (strain 2) mice as well as breeder mice that were used to maintain the colonies and generate subsequent experimental animals. Genotypes were determined by PCR. DKO (strain2) animals differed somewhat from the previously described 'strain 1' dKO (75:25C57BL/6:SV129 background) 1 mice. Unless otherwise noted all dKOs used were from strain 2. Animals housed in micro-isolater cages in a Virus Antibody Free Facility were fed a standard chow diet ad libitum.

Role of Lymphocytes in CHD of SR-BI(−/−)/ApoE(−/−) mice

Disruption of the RAG1 or RAG2 genes renders mice B- and T-cell deficient. To determine if lymphocytes play a role in the cardiac pathophysiology of SR-BI(−/−)/ApoE(−/−) mice, SR-BI(−/−)/ApoE(−/−)/RAG2(−/−) triple knockout (tKO) mice were characterized for total lymphocyte deficiency. The study was conducted on mice 36 to 45 days of age. Plasma total IgG concentrations of dKO and tKO mice were measured using the Easy-Titer® (Pierce Biotechnology, Inc., Rockford, Ill.) Mouse IgG assay kit (Product #23300) according to kit instructions. The absence of B-lymphocyte function in tKOs was confirmed by analysis of plasma levels of IgG in dKO and tKO mice. DKO mice had plasma total IgG titers similar to those of SR-BI+/+ApoE−/−Rag2+/+ control mice (0.51±0.12 vs. 0.60±0.089 mg/mL; P=0.608). Plasma total IgG titers for tKO mice and SR-BI+/+ApoE−/−Rag2−/− control mice fell below the range of detection of the assay kit used, even at sample concentrations that were 5 and 50 times higher than that used for the plasma of Rag2+/+ control mice, establishing the absence of detectable IgG in tKO mice as expected. The tKO, but not the dKO, mice did not have a fully developed thymus or normal sized lymph nodes.

Plasma Lipids and Lipoprotein Profiles of SR-BI(−/−)/ApoE (−/−)/Rag2(−/−) Mice

Plasma from animals produced as described in example 5 was obtained from blood drawn at sacrifice by centrifugation at 14,000 rpm (Spectrafuge 16M) for 10 minutes at 4° C. Lipid concentrations were determined by enzymatic assays on plasma diluted 1:4 in phosphate buffered saline (PBS) using kits (Cholesterol C-II, Free Cholesterol E and Phospholipids B) from Wako Chemical USA Inc., (Richmond, Va., USA). Plasma was diluted 1:4 in elution buffer (154 mM NaCl, 1 mM EDTA, pH 8) and subjected to FPLC analysis (total cholesterol determined for each fraction) either immediately following collection or after storage at 4° C. as described (Rigotti, et al. *Proc. Natl. Acad. Sci. U.S.A.* 94: 12610-12615 (1997)).

Disruption of the RAG2 (or RAG1) gene has been shown to lower plasma cholesterol levels in ApoE (−/−) or LDL receptor (−/−) mice. Thus, the plasma lipid levels in dKO and tKO mice were compared, because dyslipidemia (hypercholesterolemia, abnormally high unesterified to total cholesterol (UC/TC) ratio) is thought to be responsible for occlusive atherosclerosis and CHD in dKO mice. Consistent with previous reports, there was a small but significant reduction in plasma unesterified cholesterol (UC) and phospholipids in tKO animals compared to dKOs (UC (mg/dL):655±30vs.767±40 respectively; P=0.03 and phospholipids (mg/dL): 586±28vs.681±34 respectively; P=0.04), but no statistically significant differences in plasma total cholesterols (TC) (909±38vs.100±54 mg/dL respectively; P=0.17) or UC/TC ratios (Reardon, et al., *Arterioscler Thromb Vasc Biol.* 21:1011-1016 (2001); Dansky, et al., *Proc Natl Acad Sci USA* 94:4642-4646 (1997). FPLC chromatographic analysis of plasma lipoproteins revealed no major differences in the lipoprotein total cholesterol profiles (n=4 for each group) (see FIG. 7). The slightly higher amounts of cholesterol in the VLDL-size fractions from the dKO mice relative to tKO mice is similar that reported by Reardon et al. for ApoE KO mice. The minimal alterations in plasma lipoproteins by RAG2 gene disruption appear unlikely to differentially influence atherosclerosis and CHD in dKO and tKO mice.

Cardiac Histopathology of SR-BI(−/−)/ApoE(−/−)/Rag2 (−/−) Mice

The tKO animals produced in example 5 were further studied. Trichrome staining of ~6 week-old tKO hearts demonstrated extensive myocardial fibrosis similar to that in dKO mice. As in dKO mice, neutral lipid deposits as determined by oil red O staining and macrophage foam cell formation as determined by F4/80 immunohistochemical staining coincided with regions of fibrosis. The absence of CD4+ cells in the hearts of tKO mice confirmed their B- and T-cell deficiencies (RAG2 (−/−) phenotypes). Thus, neither B- nor T-cells were required for extensive fibrosis/infarction.

The lipid-rich occlusive atherosclerotic lesions in coronary arteries of tKO mice were similar to those in dKO mice. There were no significant differences in the numbers of non-occluded, partially occluded (<50% occluded) and completely occluded (>50% occluded) coronary arteries (n=4 for each group). Severely occluded arteries were prevalent in areas with myocardial fibrosis, especially near the upper ventricular outflow regions. Some occlusions contained significant cellular components; others were predominantly acellular. Thus, lymphocytes did not markedly influence the nature of the occlusive coronary disease and cardiac damage.

Cardiac Structure and Function of SR-BI(−/−)/ApoE(−/−)/Rag2(−/−) Mice

Echocardiography was used to assess cardiac function and hypertrophy in lightly anesthetized (pentobarbital, 25 mg/kg IP) dKO and tKO mice and their SR-BI positive littermate controls. M-mode and two-dimensional transthoracic echocardiography were performed on lightly sedated mice (pentobarbital, 25 mg/kg IP) using a 13-MHz linear array ultrasound transducer with the instrument adjusted for maximal frame rate (Acuson Sequoia, Siemens Medical, Mountain View, Calif.). M-mode echocardiograms were obtained at mid-left ventricle level. Two-dimensional (2D) images consisted of long-axis views of the left ventricle (LV) and short-axis images at basal, mid and apical portions of the left ventricle. The long axis length of the LV was measured from the 2D long axis view and all other measurements were performed on the short axis at the mid LV level. The fractional shortening was calculated as a measure of LV systolic function and the LV mass was calculated by the D method. The results are provided in Table 7.

No significant differences between RAG2(−/−) and RAG2(+/+) control mice were observed, therefore all controls were pooled. The values of posterior wall thickness (PWT) and LV mass (absolute and normalized to body weight) for the dKO and tKO mice were not significantly different from each other, but were greater than those of controls. The quantitative effects of CHD on the PWT seen in Table 7 are similar to those in other forms of cardiac dysfunction (Tanaka, et al., *Circulation* 94:1109-1117 (1996)).

The echocardiographically determined increases in heart size in the dKO and tKO mice were confirmed by gravimetric analysis (Table 7). Mice were weighed and euthanized by Avertin overdose. Intact hearts were removed and rinsed clean of blood with heparin/PBS (10 units/ml) (heparin sodium salt, Sigma). Whole hearts were then blotted dry and weighed using an analytical balance.

The heart-to-body weight ratios of the dKO and tKO mice were similar (P=0.2405) and 1.9- and 1.8-fold larger than for age matched controls (P<0.0001). The body weights for the dKO and tKO mice were similar (16.8±0.8 g (n=19) and 16.4±0.4 g (n=17), respectively) and smaller than that of their littermate controls (18.3±0.6 g (n=13)). The smaller size of SR-BI (−/−)/ApoE (−/−) mice compared to SR-BI-positive controls was reported previously (Braun, et al., *Circ Res.* 90:270-276 (2002)). Left ventricular fractional shortening ([LVEDD-LVESD]/LVEDD; 'FS') was used as a measure of the heart's systolic function. The mean FS for control mice was 50.1%±5.0%, corresponding to data reported by several groups for both conscious and anesthetized mice (Liao, et al., *Am J Physiol HeartCirc Physiol.* 282:H1703-1708 (2002); Gao, et al., *Cardiovasc Res.* 45:330-338 (2000); Gardin, et al., *Circ Res.* 76:907-914 (1995); Yang, et al., *Am J Physiol.* 277:H11967-1974 (1999)). There were clear defects in LV wall motion in dKO and tKO mice compared to controls. Both dKOs and tKOs had approximately 50% lower FS than control mice, demonstrating a substantial deficit in cardiac contractility. There was no significant difference in FS between the dKO and tKO mice (26.1%±6.2% vs. 24.3%±4.0%; P=0.7960). Reported FS values of approximately 10-30% for surgically-induced models of myocardial infarction and congestive heart failure as well as genetically-induced dilated cardiomyopathy, correspond well to the low values seen in the dKO and tKO mice (Liao, et al., *Am J Physiol HeartCirc Physiol.* 282:H11703-1708 (2002); Gao, et al., *Cardiovasc Res.* 45:330-338 (2000); Nishimura et al., *Science* 291:319-322 (2001)). During echocardiography both dKO and tKO mice exhibited significantly lower heart rates than those of control mice, although they did not differ from each other (395±19 vs. 386±24 bpm respectively). Numerous studies suggest that anesthesia administered before echocardiography can depress heart rate38-40 that in turn can influence echocardiographically determined parameters of cardiac function, including contractility and fractional shortening (Roth, et al., *Am J Physiol Heart Circ Physiol.* 282:H2134-2140 (2002); Takuma, et al., *Am J Physiol Heart Circ Physiol.* 280:H2364-2370 (2001)). Moreover, these effects vary with type and dosage of anesthetic and strain of mice studied (Yang, et al., *Am J Physiol.* 277:H1967-1974 (1999); Roth, et al., *Am J Physiol Heart Circ Physiol.* 282:H2134-2140 (2002); Takuma, et al., *Am J Physiol Heart Circ Physiol.* 280:H2364-2370 (2001)). However, some studies of mice undergoing conscious echocardiography demonstrate perturbations in heart rate, including bradycardia before training and tachycardia after training (Yang, et al., *Am J Physiol.* 277:H1967-1974 (1999); Roth, et al., *Am J Physiol Heart Circ Physiol.* 282:H2134-2140 (2002)). The mean heart rate for our control mice anesthetized with a low dose of pentobarbital (522±24 bpm) was similar to that measured for conscious mice during echocardiography as reported by Takuma et al. and unrestrained mice undergoing telemetry, suggesting the low dose of anesthetic used did not depress heart rate in the control mice. However, electrocardiography of dKOs has shown these mice to be hypersensitive to certain anesthetic agents (Braun, et al., *Circ Res.* 90:270-276 (2002)). Their rapid deterioration in health and short lifespans, prevent dKO mice from enduring the stress of multiple training sessions required for conscious, unanesthetized echocardiography. Previous electrocardiographic studies have shown that conscious unanesthetized dKO mice exhibit reduced heart rates as they approach the terminal stage of disease (Roselaar, et al., *Arterioscler Thromb Vasc Biol.* 16:1013-1018 (1996)). Most of the dKO and tKO mice (12/16) exhibited electrocardiographic abnormalities during echocardiographic analysis. Therefore, even if echocardiographic data were obtained without anesthesia, it is likely that the dKOs and tKOs would still have exhibited heart rates significantly lower than control mice. Given these complications, it is not possible to distinguish with certainty the effects of anesthesia from those of advanced disease on heart rate and echocardiographic data obtained from dKOs and tKOs, though it seems likely that the abnormalities observed were due, at least in part, to the underlying pathology and not solely consequences of enhanced sensitivity of these mice to anesthetics.

The Effect of Immunodeficiency on Survival of SR-BI(−/−)/ApoE(−/−)/Rag2(−/−) Mice The effect of the inactivation of the RAG2 gene on the life expectancies of these mice is shown in FIG. 8. FIG. 8 shows that the survival curves for dKO (strain 2,black) and tKO (red) mice were virtually identical (mean survival times (days): 42.0±0.5 (n=65) and 41.6±0.6 (n=35), respectively (P=0.3594 Logrank test)). RAG2 deficient mice have been reported to exhibit a normal lifespan when maintained in a pathogen-free facility such as that used here (Rideout, et al., Cell 109:17-27 (2002)). Thus, while it is possible that absence of an influence of RAG2 deficiency on survival of dKO mice could have arisen because of compensatory effects on the kinetics of the fatal pathologies normally exhibited by dKO mice and on independent processes due to the immunodeficiency, this seems unlikely. Therefore, B- and T-cells do not significantly contribute to the fatal pathophysiology in dKO mice. The survival curve of the dKO mice bred for this study (strain 2, black) significantly differed from that of the previously described SR-BI(−/−)/ApoE(−/−) dKO mice (strain 1, blue) revealing that genetic background variation can significantly impact lifespan. The mean survival of strain 1 (45.9±0.9 days, n=61) was significantly longer than that of strain 2 (P=0.0001). Remarkably, 82% of strain 2 dKOs died within an exceptionally narrow 9-day window (38-47 days of age), whereas the comparable range in strain 1 mice was 16-days (40-56 days). These differences are presumably due to their different genetic backgrounds.

TABLE 8

Echocardiographic analysis of mice on a high-fat diet which do not express SR-BI and have reduced ApoE expression (hypoE).

|  | SR-BI/hypoE normal diet (n = 6) | hypoE high-fat diet (n = 6) | SR-BI/hypoE high-fat diet (n = 9) |
|---|---|---|---|
| Heart Rate (bpm*) | 550 ± 23 | 539 ± 47 | 425 ± 27 |
| LVIDED (cm) | 0.31 ± 0.02 | 0.32 ± 0.01 | 0.32 ± 0.01 |
| LVIDES (cm) | 51 ± 2.3 | 59 ± 4.4 | 36 ± 2.3 |
| FS (%) | 51 ± 2.3 | 50 ± 4.4 | 36 ± 2.3 |
| PWT (cm) | 0.103 ± 0.005 | 0.102 ± 0.006 | 0.129 ± 0.009 |
| LV mass D3 (g) | 0.115 ± 0.008 | 0.115 ± 0.011 | 0.161 ± 0.017 |

*Values are mean ± SE.
Abbreviations used:
bpm, beats per minute;
LVIDED, left ventricular internal dimension (end diastole);
LVIDES, left ventricular internal dimension (end systole);
FS, fraction shortening;
PWT, posterior wall thickness;
LV mass, left ventricular mass.

Those skilled in the art will recognize, or be able to ascertain using no more than routine experimentation, many equivalents to the specific embodiments of the invention described herein. Such equivalents are intended to be encompassed by the following claims.

TABLE 7

Echocardiographic and gravimetric analyses

|  | FS (×100) | PWT (mm) | PWT/BW (mm/g × 100) | LV mass (Grams) | LV mass/BW (×100) | HW/BW ratio (×100) | Heart Rate (Bpm) |
|---|---|---|---|---|---|---|---|
| Control | 50.1 ± 5.0 (10) | 0.65 ± 0.03 (10) | 3.04 ± 0.19 (6) | 0.062 ± 0.006 (10) | 0.266 ± 0.015 (6) | 0.509 ± 0.010 (13) | 522 ± 24 (10) |
| dKO | 26.1 ± 6.2 (8) | 0.80 ± 0.04 (7) | 4.96 ± 0.52 (4) | 0.114 ± 0.007 (7) | 0.761 ± 0.134 (4) | 0.979 ± 0.028 (19) | 395 ± 19 (10) |
| tKO | 24.3 ± 4.0 (10) | 0.76 ± 0.03 (10) | 4.64 ± 0.15 (7) | 0.106 ± 0.013 (10) | 0.650 ± 0.094 (7) | 0.933 ± 0.026 (17) | 386 ± 24 (8) |
| P ANOVA | 0.0014 | 0.0128 | 0.0003 | 0.0019 | 0.0036 | Less than 0.0001 | 0.0002 |
| P (dKO vs. tKO) | 0.7960 | 0.4615 | 0.4688 | 0.6505 | 0.5054 | 0.2405 | 0.7774 |

FS = fractional shortening;
PWT = posterior wall thickness;
BW = gravimetric body mass;
HW = gravimetric heart mass.
Results for RAG2(+/+) and RAG2(−/−) SR-BI-positive littermates of dKO and tKO mice were combined as controls.
N in parentheses.
P ANOVA all three groups;
P (dKO vs. tKO) from unpaired student's t-test.
P ≦ 0.05 was considerd significant.
Values are expressed as mean ± SEM.

Cardiac function was assessed in wild type, hypoE, SR-BI−/− and SR-BI/hypoE mice after being fed the high-fat diet using electrocardiography and echocardiography (Table 8). Normal electrocardiography (ECG) patterns were seen in wild type, hypoE, and SR-BI−/− mice while cardiac dysfunction was observed in SR-BI/hypoE mice. Following analysis using echocardiography, SR-BI/hypoE mice displayed increased heart wall thickness, increased LV (left ventricular) internal dimension at end systole (LVIDES), and reduced fractional shortening indicating contractile dysfunction. These data are summarized in Table 5. The electrocardiography and echocardiography results demonstrate that SR-BI/hypoE mice fed a high-fat diet have impaired heart function.

We claim:

1. A transgenic mouse model of coronary heart disease wherein a heart attack can be induced by feeding a lipid enriched diet, comprising a mouse genetically engineered to knock out expression of active SR-BI, and having apolipoprotein E activity or expression decreased to 2-5% of normal levels, wherein feeding the mouse a lipid rich diet induces a heart attack in the mouse.

2. The mouse model of claim 1 wherein the apolipoprotein E activity or expression is decreased by a method selected from the group consisting of administering small molecules, administering antibodies, transgene expression, and alteration of a heterologous regulatory gene.

3. The mouse model of claim 2 wherein the transgene expression is for siRNA.

4. The mouse model of claim 1 wherein the heart attack is induced by altering the diet of the animal.

5. The mouse model of claim 1 comprising the animal housed alone or in groups and fed a high fat diet.

6. A method for screening for compounds having an effect on disorders selected from the group consisting of cardiac fibrosis, myocardial infarction, defects in electrical conductance, atherosclerosis, unstable plaque, heart failure, infertility, reduced life span, abnormal red blood cell development, abnormal apolipoprotein metabolism, stroke or diseases associated with abnormal cardiac structure or function or elevated cholesterol or lipoprotein levels comprising administering the compound to a mouse genetically engineered to knockout expression of active SR-BI, and having apolipoprotein activity or expression decreased to 2-5% of normal levels and determining the effect on the disorder in the treated mouse relative to control mouse not treated with the compound.

7. The method of claim 6 wherein the apolipoprotein is ApoE.

8. The method of claim 6 wherein a compound which lowers the level or alters the function of apolipoprotein is administered to the mouse.

9. The method of claim 6 wherein the mouse is housed alone or in groups, further comprising screening for an effect of housing alone or in groups, on the efficacy of the compound.

10. The method of claim 6 wherein the compound is administered before, during or after changing the diet of the mouse to a lipid enriched diet.

11. A method for making a mouse for screening for compounds affecting the symptoms of a disorder selected from the group consisting of cardiac fibrosis, myocardial infarction, defects in electrical conductance, atherosclerosis, unstable plaque, heart failure, infertility, reduced life span, abnormal red blood cell development, abnormal apolipoprotein metabolism, stroke or diseases associated with abnormal cardiac structure or function or elevated cholesterol or lipoprotein levels comprising knocking out the SR-B1 in a mouse and decreasing apolipoprotein activity or expression to 2-5% of normal levels in the mouse.

12. The method of claim 11 wherein the apolipoprotein is apolipoprotein E.

13. A transgenic mouse whose genome comprises a homozygous disruption of an endogenous SR-BI and an Arg-61 allelic variant of mouse ApoE, wherein the mouse does not produce functional SR-BI and produces approximately 5% of normal ApoE mRNA.

14. The transgenic mouse of claim 13 wherein feeding the mouse a lipid rich diet induces a heart attack in the mouse.

15. A method for screening for compounds having an effect on disorders selected from the group consisting of cardiac fibrosis, myocardial infarction, defects in electrical conductance, atherosclerosis, unstable plaque, heart failure, infertility, reduced life span, abnormal red blood cell development, abnormal apolipoprotein metabolism, stroke or diseases associated with abnormal cardiac structure or function or elevated cholesterol or lipoprotein levels comprising
　　administering the compound to animals which are deficient in fully active SR-BI and has a hypomorphic apolipoprotein activity, and determining the effect on the disorder in the treated animals relative to control animals not treated with the compound,
　　wherein the animal is a transgenic mouse whose genome comprises a homozygous disruption of an endogenous SR-BI and an Arg-61 allelic variant of mouse ApoE,
　　wherein the mouse does not produce functional SR-BI and produces approximately 5% of normal ApoE mRNA.

16. A method for making an animal for screening for compounds affecting the symptoms of a disorder selected from the group consisting of cardiac fibrosis, myocardial infarction, defects in electrical conductance, atherosclerosis, unstable plaque, heart failure, infertility, reduced life span, abnormal red blood cell development, abnormal apolipoprotein metabolism, stroke or diseases associated with abnormal cardiac structure or function or elevated cholesterol or lipoprotein levels comprising genetically engineering the SR-BI and apolipoprotein activity in an animal, wherein the animal is a transgenic mouse whose genome comprises a homozygous disruption of an endogenous SR-BI and an Arg-61 allelic variant of mouse ApoE, wherein the mouse does not produce functional SR-BI and produces approximately 5% of normal ApoE mRNA.

* * * * *